United States Patent
Amblard et al.

(10) Patent No.: US 9,259,581 B2
(45) Date of Patent: Feb. 16, 2016

(54) ACTIVE IMPLANTABLE MEDICAL DEVICE WITH DUAL CHAMBER PACING FOR THE TREATMENT OF HEART FAILURE WITH PRESERVED EJECTION FRACTION

(71) Applicant: SORIN CRM SAS, Clamart (FR)

(72) Inventors: Amel Amblard, Chatenay Malabry (FR); Marcel Limousin, Paris (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 14/559,793

(22) Filed: Dec. 3, 2014

(65) Prior Publication Data
US 2015/0165198 A1 Jun. 18, 2015

(30) Foreign Application Priority Data
Dec. 4, 2013 (FR) ...................................... 13 62123

(51) Int. Cl.
| | |
|---|---|
| *A61N 1/00* | (2006.01) |
| *A61B 5/02* | (2006.01) |
| *A61B 5/04* | (2006.01) |
| *A61N 1/368* | (2006.01) |
| *A61N 1/362* | (2006.01) |

(52) U.S. Cl.
CPC .............. *A61N 1/368* (2013.01); *A61N 1/3627* (2013.01)

(58) Field of Classification Search
USPC .......................................................... 607/27
See application file for complete search history.

(56) References Cited

U.S. PATENT DOCUMENTS 8,583,234 B1 11/2013 Muller
2003/0097158 A1* 5/2003 Belalcazar ......... A61N 1/37252
607/32

FOREIGN PATENT DOCUMENTS

EP 2 471 575 7/2012
WO WO-2010/071849 6/2010

OTHER PUBLICATIONS

Eicher et al., "Permanent left atrial pacing therapy may improve symptoms in heart failure patients with preserved ejection fraction and atrial dyssynchrony: a pilot study prior to a notional clinical research programme", European Journal of Heart Failure, Elsevier, Amsterdam, NL, vol. 15, No. 1, Jan. 1, 2013, pp. 85-93.
Foreign Search Report for French Patent Application No. FR 1362123, dated Apr. 2, 2014, 2 pages.

* cited by examiner

*Primary Examiner* — Nicole F Lavert
(74) *Attorney, Agent, or Firm* — Foley & Lardner LLP

(57) ABSTRACT

An active implantable medical device provides atrial stimulation for resynchronization of the heart chambers. After a first cycle without stimulation, a premature left atrial stimulation is delivered with application of a short left inter-atrial delay, shorter than the sinus rhythm coupling interval. During the next cycle a non-premature left atrial stimulation is delivered, and the atrioventricular interval between the left atrial depolarization and the ventricular depolarization is evaluated and compared to its value in sinus rhythm to modify as necessary a parameter of the left atrial stimulation, such as the short left inter-atrial delay.

20 Claims, 4 Drawing Sheets

ACTIVE IMPLANTABLE MEDICAL DEVICE WITH DUAL CHAMBER PACING FOR THE TREATMENT OF HEART FAILURE WITH PRESERVED EJECTION FRACTION

CROSS REFERENCE TO RELATED APPLICATIONS

This application claims the benefit of and priority to French Patent Application No. 1362123, filed Dec. 4, 2013, which is hereby incorporated by reference herein in its entirety.

BACKGROUND

The invention relates to "active implantable medical devices" as defined by Directive 90/385/EEC of 20 Jun. 1990 of the Council of the European Communities, specifically implants to continuously monitor heart rhythm and deliver if necessary to heart electrical pulses for stimulation, resynchronization and/or defibrillation in case of rhythm disorder detected by the device. The invention more particularly relates to devices for treating heart failure (HF), as an alternative or in addition to the treatment of cardiac rhythm disorders.

This therapy is designed to resynchronize the contraction of the heart chambers (atrium and ventricle, and between the two ventricles) so as to improve the patient's condition by optimizing the phases of the hemodynamic cycle. The cycle includes pre-ejection, isovolumetric contraction, systolic ejection, isovolumetric relaxation and finally filling of the cavity.

Most of these devices implement a technique called "CRT" (Cardiac Resynchronization Therapy) or "BVP" (Bi-Ventricular Pacing) for delivering electrical pulses as necessary to ensure joint and continuous stimulation of the two ventricles, left and right, to resynchronize them. This biventricular resynchronization technique however addresses only one of the forms of heart failure, known as "systolic failure". In this form of the disease, the heart muscle is unable to provide the force necessary to ensure adequate cardiac output, and the patient shows signs of expansion resulting in a delay of left ventricular depolarization. CRT Biventricular pacing is then used to resynchronize the ventricles and make cardiac contraction more uniform.

In the other form of heart failure called "diastolic failure" or "preserved ejection fraction heart failure" (HFpEF, Heart Failure with preserved Ejection Fraction), there is no desynchronization of the ventricles; it comes from a failure in the left ventricular filling. Biventricular CRT stimulation will be ineffective in this case. But this condition affects about 40% of heart failure patients, and there is no known effective treatment to remedy to it.

This form of disease in some patients may be the result of a disorder of conduction in the atria (inter-atrial block), which delays the depolarization, and therefore the contraction of the left atrium (OG) with respect to the right atrium (OD). However, as atrioventricular conduction pathways are not altered, depolarization and contraction of two the right (VD) and left (VG) ventricles occur within a reasonable time, without synchronization VD-VG. It is between the contraction of the left atrium and that of the left ventricle that the inter-atrial block OD-OG generates a poor sequencing OG-VG. The delay of the contraction of the left atrium has for consequence that it contracts substantially at the same moment as the left ventricle, and therefore cannot properly fulfill its function and contribute to the left ventricular active filling.

To treat this heart failure with preserved ejection fraction and pathology, a technique of atrial overdriving including stimulating the left atrium to a frequency slightly above the spontaneous sinus rhythm frequency (i.e. the rate of the right atrium) has been proposed, thereby systematically causing premature depolarization of the left atrium and thereby restoring a more normal OG-VG sequence.

Specifically, in this known technique, the device regularly measures the spontaneous rhythm of the patient and applies a sequence of pacing pulses at a slightly faster rate, arbitrarily programmed to cause a prematurity in the order of 50 to 100 ms compared to an atrial coupling interval corresponding to the spontaneous sinus rhythm. After several cycles at this accelerated pace, the frequency gradually slows until reappearance of spontaneous activity, then the overdriving method is repeated in the same way and so on.

The applied stimulation frequency thus varies continuously between values wherein it is too fast (overdriving period) or too slow (period of reappearance of spontaneous rhythm, with OD-VD synchronization), without real monitoring of the effectiveness of a possible return to a proper synchronization of the left cavities.

This pacing mode may also interfere with the filling of the right cavities. In fact, due to premature stimulation of the left atrium, the OD-VD synchronization is significantly altered in a manner which may be incompatible with satisfactory filling of the right ventricle (these aspects will be clarified in the detailed description). Improvement therapy in the left ventricular filling is thus likely to induce adverse effects on the filling of the right ventricle, so in the cavity that was not affected by the pathology to be treated.

Another technique is described in EP 2471575 A1 (Sorin CRM SAS) which, in particular to overcome these drawbacks, implements a sensor for collecting a endocardial acceleration signal (EA). The EA signal is analyzed to detect the presence of a specific component reflecting the atrial contraction (EA4 component) and to identify the moment of occurrence of this component. If the EA4 component is present, this means that the sequencing of atrial contractions is correct because otherwise (left atrial contractions too late), the EA4 component would be masked in the component of the EA signal corresponding to the immediately following ventricular contraction (EA1 component). The inter-atrial stimulation interval (AA interval) is then dynamically adjusted depending on the result of this analysis. However, this technique requires an implantable lead provided with an implanted endocardial acceleration sensor, and a generator capable of processing the signals delivered by such an EA sensor.

A similar technique is disclosed by U.S. Pat. No. 8,583,234 B1, which proposes in addition, after a first cardiac cycle without left atrial pacing, to deliver an overdriving pulse during a second immediately consecutive cardiac cycle.

The exemplary embodiments herein propose a technique for treatment of heart failure with preserved ejection fraction in patients with inter-atrial mechanical delay, which overcomes the drawbacks of the methods proposed so far and which does not require the use of means for collecting and analyzing an EA signal.

Exemplary embodiments also propose a technique that ensures recovery of diastolic function in a method that is simple (in terms of resources used) and very reactive (efficiency obtained cycle to cycle), allowing the patient to recover a satisfactory OG-VG sequencing (sequencing of left atrial contraction relative to that of the left ventricle), so that the atrium can correctly perform its filling function completion for the left ventricle.

Exemplary embodiments are directed to a conventional dual chamber device (with left atrial detection/stimulation and ventricular detection, but without detection of depolarization signals of the right atrium), and this simply by reprogramming the control circuits of this device (e.g., without hardware modification).

SUMMARY

Specifically, the exemplary embodiments provide a device including digital processor circuits configured for collecting ventricular depolarizations; for collecting left atrial depolarizations; delivery of left atrial pacing pulses; and for atrial stimulation, able to selectively output the left atrial pacing pulses prematurely, by applying a short left inter-atrial delay, shorter than the coupling interval of sinus rhythm.

After a first cardiac cycle without left atrial pacing, the control means deliver a premature left atrial pacing pulse during a second immediately consecutive cardiac cycle, with application of a short left atrial delay, shorter than the coupling interval of sinus rhythm.

As a feature of the invention, the atrial pacing control means further operate so as to:

output a not premature left atrial stimulation pulse during a third cardiac cycle immediately subsequent to the second cardiac cycle, with application of a left inter-atrial delay corresponding to the coupling interval of the sinus rhythm; and assess the atrioventricular interval between the left atrial depolarization and the ventricular depolarization during the second and third cardiac cycles, or the interventricular delay between two successive ventricular depolarizations, and then compare the atrioventricular delay thus evaluated to the atrioventricular delay in sinus rhythm or the interventricular delay thus evaluated to the interventricular delay in sinus rhythm. The control means then modify, if necessary, at least one parameter of the atrial pacing control methods, such as the short left inter-atrial delay, depending on the result of the comparison.

According to various advantageous subsidiary characteristics:

If the atrioventricular delay increases beyond a given target value, or if the interventricular delay is less than the coupling interval of sinus rhythm, it is planned to reduce from one variation step the short left inter-atrial delay; then to deliver a premature left atrial stimulation pulse during a subsequent cardiac cycle, with the application of the short left inter-atrial delay reduced by one step;

Conversely, if the atrioventricular interval does not increase beyond the target value and the interventricular delay remains close to the coupling interval of sinus rhythm, it is planned to increase from one variation step the short left inter-atrial delay; then to deliver a left atrial premature stimulation pulse during a subsequent cardiac cycle, with the application of the short left inter-atrial delay increased by one step;

The device further includes means able, upon detection of a predetermined event, to: inhibit the issuance of any of the left atrial pacing pulses during at least one cardiac cycle; measure on at least one cardiac cycle the ventricular coupling interval; and store this ventricular coupling interval as the coupling interval of sinus rhythm to determine the short left inter-atrial and left inter-atrial delays corresponding to the coupling interval of sinus rhythm, in the subsequent cycles;

This predetermined event is the expiry of a predetermined fixed delay, or the detection of the crossing of a predetermined threshold by the atrioventricular delay variation and/or by the atrial coupling interval and/or by the interventricular delay;

The device further includes means for sensing right atrial depolarizations, and means adapted to evaluate the variation of the atrioventricular delay separating the atrioventricular delay from the right atrial depolarization from one cardiac cycle to the next one(s), and if the variation thus evaluated exceeds a predetermined threshold, to reduce from one variation step the short left inter-atrial delay.

In an exemplary embodiment, a method for resynchronization of the contraction of the heart chambers includes sensing ventricular depolarizations, sensing left atrial depolarizations, and controlling atrial stimulation to prematurely selectively output the left atrial pacing pulses, by applying a pacing pulse at a short left inter-atrial delay, shorter than the coupling interval of sinus rhythm according to a stimulation protocol. The stimulation protocol includes, after a first cardiac cycle without left atrial pacing (Cycle 2), delivery of a premature left atrial stimulation pulse during a second immediately consecutive cardiac cycle (Cycle 3), with application of a short left inter-atrial delay (D2) shorter than the coupling interval of sinus rhythm (D1) and delivery of a non-premature left-atrial stimulation pulse during a third cardiac cycle (cycle 4) immediately subsequent to the second cardiac cycle (Cycle 3), with application of a left inter-atrial delay (D2) corresponding to the coupling interval of sinus rhythm. The method further includes assessing the atrioventricular interval between left atrial depolarization and ventricular depolarization during the second and third cardiac cycles, or the interventricular delay between two successive ventricular depolarizations. The method further includes comparing the atrioventricular interval thus evaluated to the atrioventricular interval in sinus rhythm, or the interventricular delay thus assessed to the interventricular delay in sinus rhythm. The method further includes modifying, if necessary, at least one parameter of the stimulation protocol according to the result of the comparison.

In an exemplary embodiment, a cardiac resynchronization system, includes a first stimulation/detection electrode for positioning in a ventricle of a heart and a second stimulation/detection electrode for positioning in the left atrium of the heart. The electrodes are configured to be coupled to an implantable medical device, the implantable medical device comprising a generator and digital processor circuits. The digital processor circuits are configured to sense ventricular depolarizations from the first stimulation/detection electrode and sense left atrial depolarizations from the second stimulation/detection electrode. The digital processor circuits are further configured to deliver, by the generator, a left atrial stimulation pulse during a cardiac cycle immediately following a preceding cardiac cycle with no left atrial stimulation, the left atrial stimulation pulse delivered at an inter-atrial coupling interval. The inter-atrial coupling interval is a short left inter-atrial delay shorter than the sinus rhythm inter-atrial coupling interval. The digital processor circuits are further configured to deliver a second left-atrial stimulation pulse during an immediately subsequent cardiac cycle at an inter-atrial coupling interval corresponding to the sinus rhythm coupling interval. The digital processor circuits are further configured to assess the atrioventricular interval between left atrial depolarization and ventricular depolarization during the second and third cardiac cycles, or the interventricular delay between two successive ventricular depolarizations, and compare the atrioventricular interval thus evaluated to the atrioventricular interval in sinus rhythm, or the interventricular delay thus assessed to the interventricular delay in sinus rhythm. The digital processor circuits are further configured to modify, if necessary, the inter-atrial coupling interval according to the result of the comparison.

BRIEF DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

An embodiment of the device of the invention will now be described. Regarding its software aspects, the invention may be implemented by appropriate programming of the controlling software of a known stimulator, for example a cardiac pacemaker, resynchronizer or defibrillator, including methods of acquisition of a signal provided by endocardial leads.

The invention may notably be applied to implantable devices, such as that of the Reply, Ovatio and Paradym families, manufactured and commercialized by Sorin CRM, Clamart, France. These devices include programmable microprocessor circuitry to receive, format and process electrical signals collected by implantable electrodes, and deliver stimulation pulses to these electrodes. It is possible to download in it by telemetry software that is stored in memory and executed to implement the functions of the invention that are described below. The adaptation of these devices to the implementation of the functions of the invention is within the skill in the art and will not be described in detail.

Figure 1:
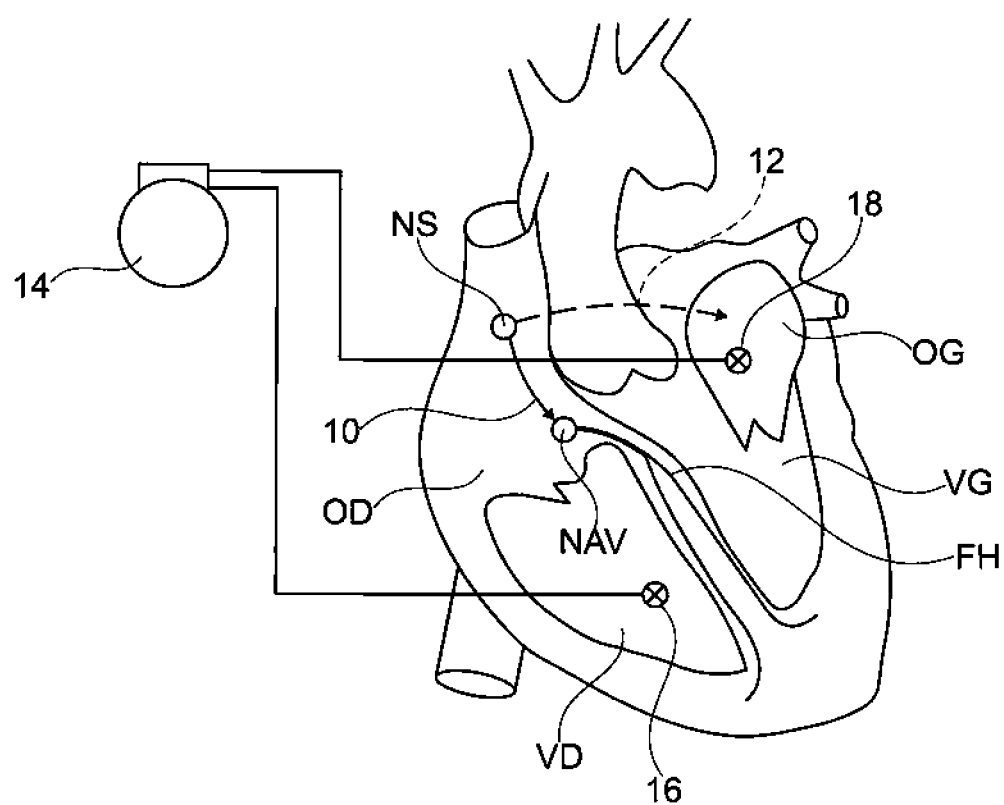
FIG. 1 schematically illustrates the position of the different sites involved in spontaneous or stimulated cyclic electrical activity of the heart.

FIG. 1 shows a diagram of the heart with its four chambers: right atrium OD, right ventricle VD, left atrium OG and left ventricle VG. The coordinated contraction of the various cavities is initiated in the sinus node NS, then the depolarization wave is conducted to the atrioventricular node NAV (conduction represented by arrow 10) and from this node to the His bundle FH, and finally to tissues of right and left ventricles VD and VG, causing contraction thereof. Moreover, the depolarization wave delivered by the sinus node NS causes contraction of the right atrium OD and, after inter-atrial conduction (conduction represented by arrow 12) to the left atrium OG, causes contraction of the left atrium.

In the case of a patient suffering from heart failure with preserved ejection fraction, the atrioventricular conduction (arrow 10, from the sinus node NS to the atrioventricular node NAV) is usually preserved, as well as the conduction paths to ensure synchronous contraction of both left and right ventricles VD and VG. However, when the inter-atrial conduction (arrow 12) is altered, it causes a delay in the depolarization and, therefore, the contraction of the left atrium OG compared to the ventricles. This induces a poor timing of the contraction of the left atrium OG relative to the left ventricle VG with a more or less concomitant contraction of the two cavities. Therefore, the left atrium OG cannot properly fulfill its function, which is to complete the filling of the left ventricle VG.

The implantable device 14 includes a generator connected to a ventricular detection (or stimulation/detection) electrode 16, for example an electrode carried by an endocardial lead housed in the right ventricle VD. It also includes a stimulation/detection electrode 18 positioned at the left atrium OG, for example carried by an electrode positioned in a coronary sinus or in a vein of the coronary network such as the Marshall vein, or the atrial septum, or of course on the inter-atrial septum or directly in the left atrium after inter-atrial septal puncture.

Figure 2:
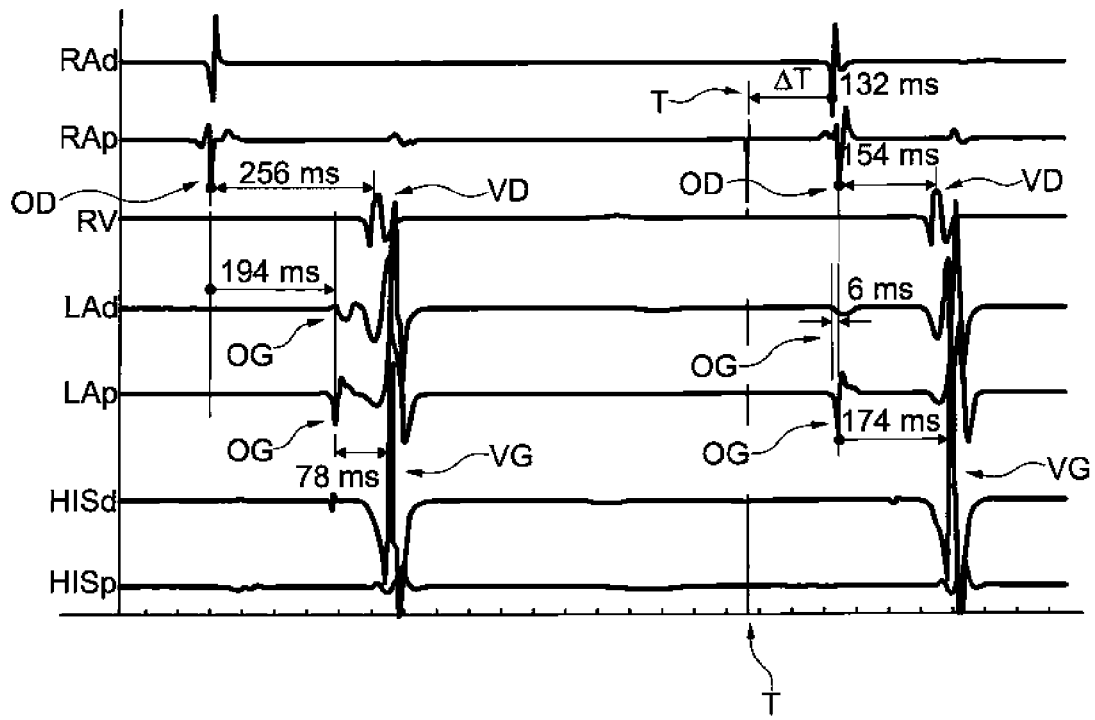
FIG. 2 is a series of timing diagrams illustrating various signals characterizing cardiac activity during two successive cycles, in the case of a currently used overdriving technique.

The conventional technique of overdriving usually implemented with this type of device to remedy a heart failure with preserved ejection fraction is illustrated in FIG. 2. Plots of the various records collected during two successive cardiac cycles are shown in this figure, the first in spontaneous rhythm and the second with overdriving. These records correspond to the following branches: distal and proximal electrodes on the right atrium (RAd and RAp), the right ventricle (RV), distal and proximal electrodes on the left atrium (LAd and LAp), and distal and proximal electrodes on the His bundle (HISd and HISp), roughly corresponding to the depolarization of the left ventricle (including the HISd branch).

At the first cardiac cycle, there is a compliant delay of 256 ms between the spontaneous depolarization of the right ventricle (VD) and the depolarization of the right atrium (OD). By contrast, the OD-OG delay between the respective depolarization of both atria has a value, excessive and pathological, of 194 ms, which has the effect of leaving a gap of 78 ms between the depolarization of the left atrium (OG) and the contraction of the left ventricle (VG), an interval too short to provide adequate filling of the left ventricle. In extreme cases, the contraction of the left atrium and of the left ventricle can even be almost concurrent, negating the role of the atrium in the filling of the ventricle.

In the second cardiac cycle, which is a cycle with overdriving, the device paces the left atrium at a given instant (T) having a deliberate prematurity ΔT from the normal sinus rhythm corresponding to the ventricular coupling interval from a cycle to the next. This premature stimulation of the left atrium will reset an almost physiological sequencing OG-VG (174 ms). However, the OD-VD sequencing is significantly changed, since this delay is now 154 ms instead of 256 ms. When this reduction is significant, it can lead to detrimental effects regarding the hemodynamic system in the right side.

Figure 3:
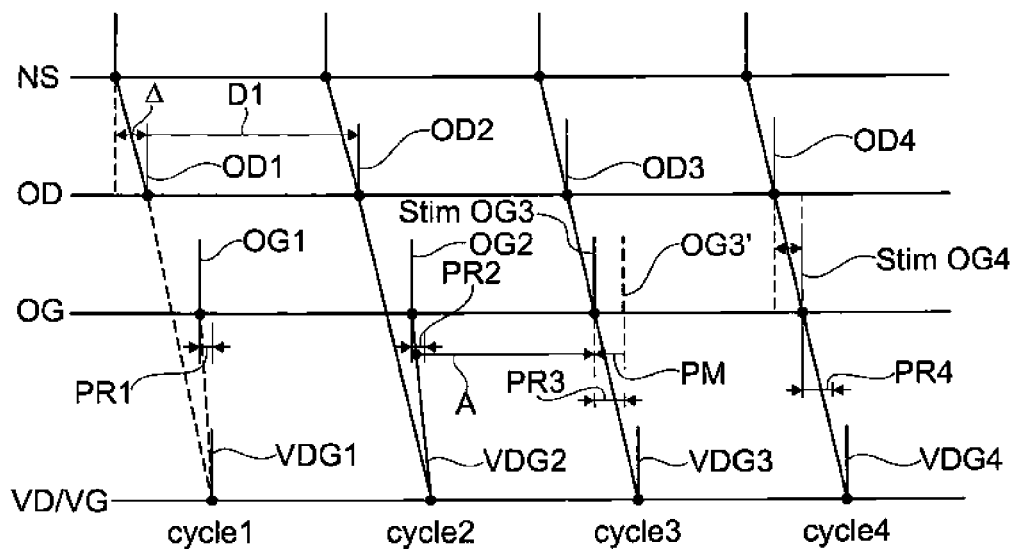
FIG. 3 is a diagram illustrating, in one exemplary embodiment, the sequencing of atrial and ventricular detection and stimulation in four successive cardiac cycles, in the case of a device operating according to the teachings of the invention.

FIG. 3 is a diagram illustrating the sequencing of atrial and ventricular detection and stimulation in four successive cardiac cycles, in the case of a device operating according to the teachings of the invention. Various markers are represented in the diagram, corresponding to the sinus rhythm NS, the right atrial rhythm OD (not accessible to measurement), the left atrial rhythm OG (detected by the electrode 18), and the ventricular rhythm VD/VG (detected by the electrode 16; it is assumed that there is no delay between the depolarization of the right ventricle and of the left ventricle).

The basic principle of the invention is to control the device with controlled stimulation of the left atrium to avoid overdriving effect and thus not to change the right atrioventricular sequence.

Initially (Cycle 1), the initial influx originating in the sinus node propagates through the right atrium. The OD1 marker corresponds to a detection that would be issued by a right atrial lead with a delay Δ from the beginning of the cycle, a delay corresponding to the propagation delay to the right atrium from the sinus node.

This influx then depolarizes the atrioventricular node and reaches the ventricles (VDG1 marker). It also propagates to the left atrium (OG1 marker), with a significant delay in the pathology of heart failure with preserved ejection fraction, so that in the shown example, the depolarization of the left atrium (OG1 marker) and that of the ventricles (VDG1 marker) are substantially concurrent.

The cycle repeats (Cycle 2), with an atrial coupling interval D1 corresponding to sinus rhythm. The sequencing default of the left atrium recurs, with a too long D2 interval between depolarization of the right (OD2 marker) and left (OG2 marker) atria.

At the next cycle (cycle 3), in accordance with the invention, a stimulation is delivered to the left atrium (StimOG3 marker) after a delay A from the previous depolarization of the left atrium (OG2 Marker). This delay is chosen to generate a predetermined PM prematurity (relative to the OG3' marker of the depolarization that would have occurred with the normal atrial coupling interval), calculated:

To ensure that the OG3-VDG3 interval is long enough to establish a normal sequencing of the left cavities, and Not to change the OD3-VDG3 sequencing of the right cavities (this information being not assessable by the device unless it is of the "triple chamber" type, with a right atrial lead).

To do this, the device determines the duration PR1 (OG1–VDG1) and PR2 (OG2–VDG2) during cycles 1 and 2, and calculates a prematurity such that the inter-atrial interval AA is given by:

$$AA=RR-PM,$$

RR being the ventricular coupling interval (detected by the ventricular electrode 16), and PM being a fixed or programmable time interval, e.g. 150 ms.

During the next cycle (Cycle 4) the device delivers to the left atrium stimulation (StimOG4 marker), but with a D3 inter-atrial delay corresponding to the coupling interval RR that was measured during cycles 1 and 2.

The device then measures the interval PR3 (OG3–VDG3) and compares this interval to the interval PR1 (measured interval OG1–VDG1 which can alternatively be replaced by a programmable target value corresponding to the expected value of the coupling interval in sinus rhythm):

If PR3<PR1+PM, this means that prematurity is sufficient and that the OG-VG sequence is restored. A second check may be made by checking the stability of the interval RR3 versus RR1;

If RR3<RR1, this means either that the pace has accelerated, or that the prematurity was too significant. A retest is then performed with a lower prematurity PM (reduced by one step, typically 8 ms) to find a sequence n such that the interval PRn=PR1;

In the case where a programmable target value is used, as described above, if the atrioventricular interval does not increase beyond the target value and the interventricular delay interval remains near of the sinus rhythm coupling interval, the short left inter-atrial delay should then be increased by one step and then deliver a premature left atrial stimulation pulse in a subsequent cycle, with application of this delay increased by one step.

On a regular basis, e.g. every minute, or in case of significant changes in the PR atrioventricular interval or RR ventricular coupling interval exceeding a given threshold, the above method is repeated in order to dispose of a cycle without stimulation of the left atrium, which serves as a reference.

In the event of a "triple chamber" device equipped with methods for sensing right atrial depolarizations, it is possible to evaluate the change in the right atrioventricular delay from one cycle to the other(s), a variation that would reveal, beyond a certain threshold, a negative impact of overdriving and should lead to reduce the prematurity initially applied.

Figure 4:
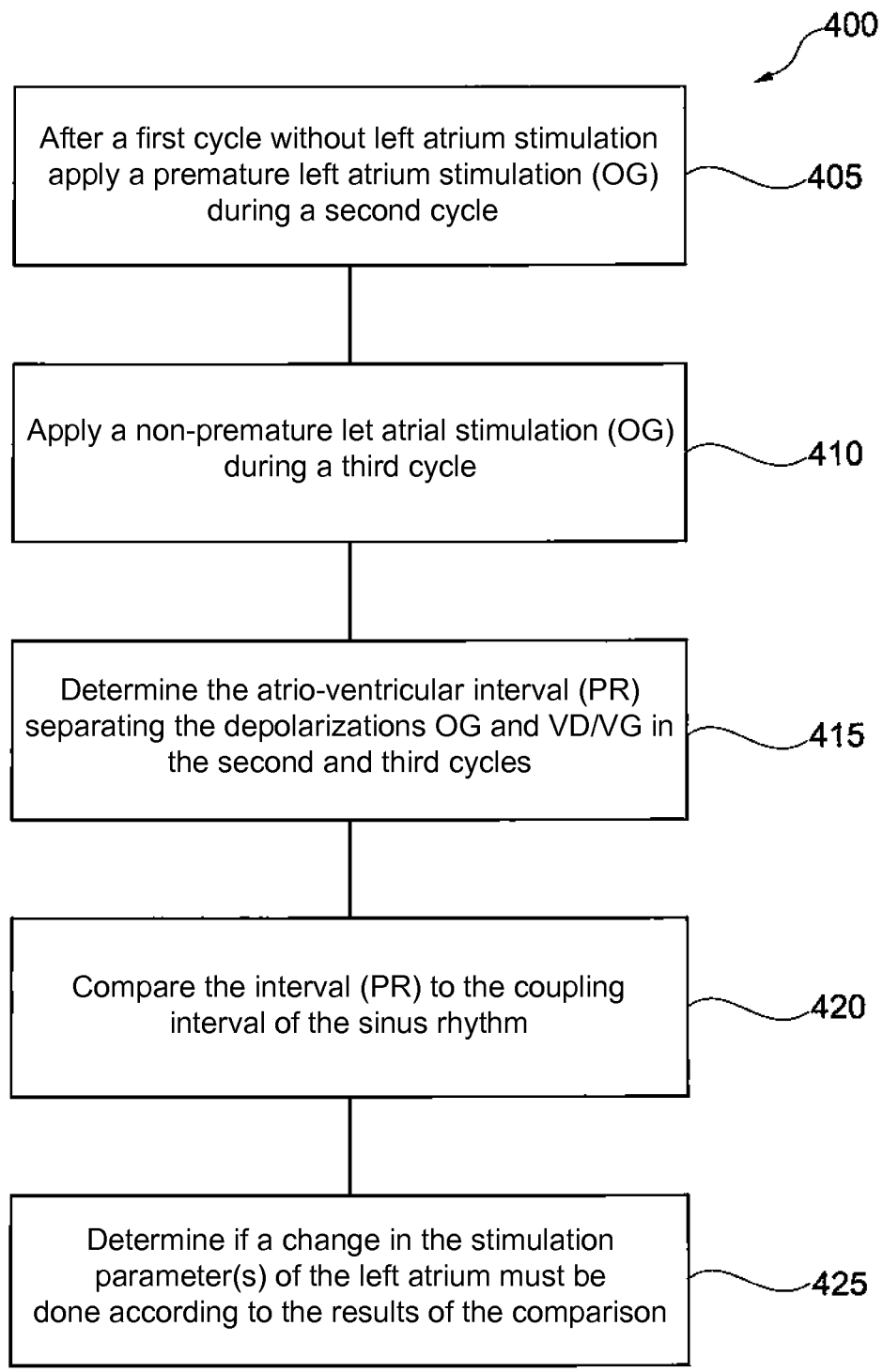
FIG. 4 is a flowchart describing the method to deliver cardiac pacing according to an embodiment of the invention.

A block diagram of a flowchart 400 of delivery of cardiac pacing according to an exemplary embodiment of the invention is shown in FIG. 4. After a first cardiac cycle in which no left atrial pacing OG is delivered, the device (e.g., an implantable medical device) delivers a premature stimulation pulse OG during the second cardiac cycle (step 405) that immediately follows the first cardiac cycle. The premature stimulation OG is adjusted to cause the application of a short left inter-atrial delay, shorter than the coupling interval of sinus rhythm. The device then applies a not premature pacing pulse OG during a third cardiac cycle (step 410), which immediately follows the second cardiac cycle. The not premature stimulation pulse OG is adjusted so as to cause the application of a left inter-atrial delay which corresponds to the coupling of the sinus period.

The device then determines an atrioventricular delay (PR interval) between the depolarization of the left atrium and that of the ventricles in the second and third cycles (step 415). The device compares the atrioventricular delay PR to the coupling interval of sinus rhythm (step 420). Depending on the result of the comparison, the device determines, if necessary, how to modify one or more parameters of the stimulation applied to the left atrium during subsequent cardiac cycles (step 425). One or more steps of the flowchart 400 may be repeated after changing of the settings, to further modify the parameters and/or to optimize the stimulation of the left atrium.

Figure 5:
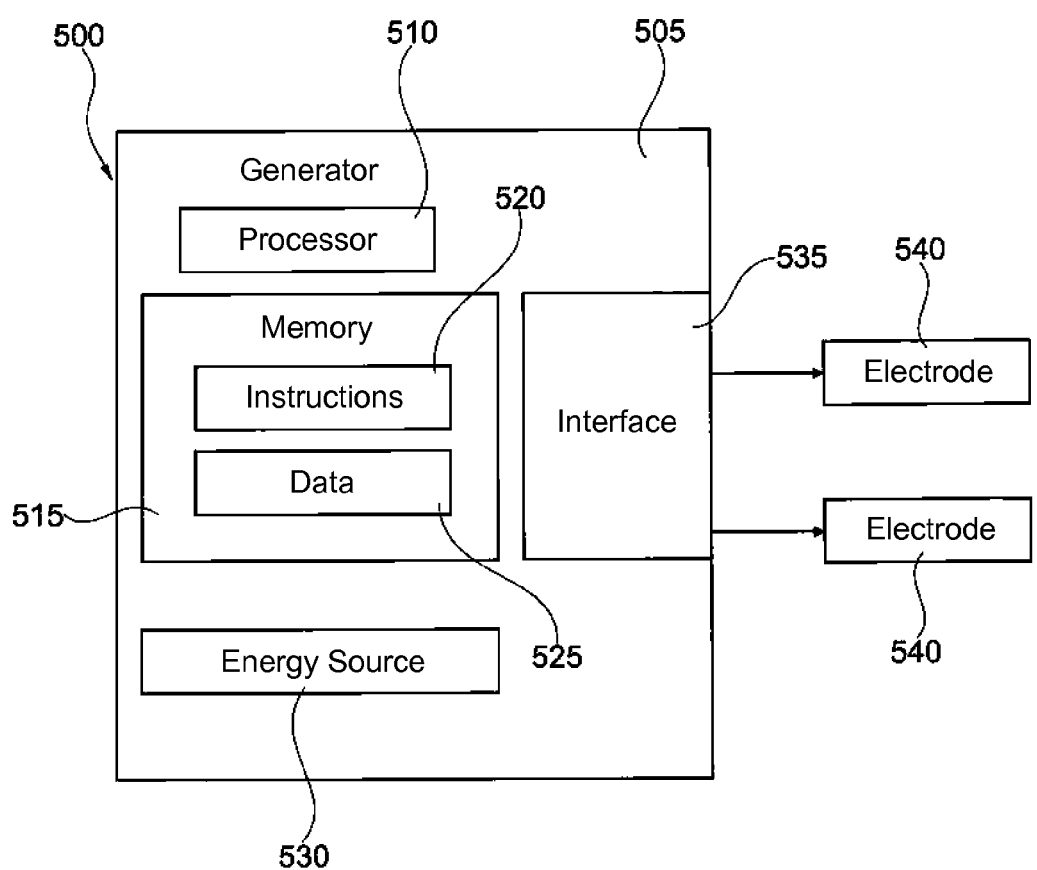
FIG. 5 is a block diagram illustrating an embodiment of an implantable medical device that can be used to implement various features presented herein.

A block diagram of an exemplary embodiment of a device 500 that can be used to implement various features described above is shown in FIG. 5. The device 500 may be an implantable medical device adapted for implantation in a subject, e.g. a patient. The device 500 includes a generator 505 configured to generate stimulation signals to tissue, for example a cardiac tissue, nerve tissue, etc. Detection signals can be received from one or more electrodes 540 coupled to generator 505 via wire 535 or a wireless interface. In some embodiments, the generator 505 can be connected to the electrodes 540 by cables. Also, in some embodiments the generator 505 may be connected to electrodes and include a power source such as a battery 530. In some embodiments, the generator 505 may include one or more wireless transceivers configured to allow the generator 505 to communicate wirelessly with one or more other devices (e.g., devices external to the patient). For example, a wireless transceiver may communicate with a computing device for general purpose or special purpose (e.g., a desktop computer, a tablet, etc.), particularly in a hospital or in a clinical environment for transmitting signals to and from the external computer device, for example to receive control signals configured for controlling the detection/stimulation settings for the generator 505 and/or provide data relating to the detection/stimulation to the external computing device.

The generator 505 includes a processor 510 and a memory 515. The processor 510 can be of any standard type or a processor for special purposes that may be integrated into the housing of the generator 505. The memory 515 can include any appropriate type of storage medium readable by a machine for storing machine-executable instructions 520 machine and/or other data 525. The instructions 520 can be executed by the processor 510 to implement various operations described in this paper. For example, such storage media readable by a machine may include RAM, ROM, EPROM, EEPROM, flash memory or any other methods which can be used to transfer or store program code in the form of machine executable instructions or of data structures that can be read by a machine with a processor. Any combination of the above is also included in the scope of what is referred to as a storage medium readable by machine. The machines or computer-readable storage supports mentioned here do not include the temporary supports, such as signals in free field.

In some embodiments, the memory 515 may include one or more modules with instructions configured to cause the processor 510 to perform various functions such as those described above. For example, the memory 515 may include a stimulation module configured to control the generation and/or transmission of stimulation pulses (e.g. the atrial pacing pulses) to electrodes 540. The memory 515 may include a module configured to detect the information collected by the electrodes 540 and assess the response to be provided (for example, assessing the atrial coupling interval and/or comparing the right atrial coupling interval and the sinus rhythm interval). The detection unit may be configured to modify one or more parameters of the stimulation depending on this evaluation. The parameters can also be stored in the memory 515.

The invention claimed is:

1. An active implantable medical device, the device comprising digital processor circuits configured to:
    sense ventricular depolarizations;
    sense left atrial depolarizations;
    deliver left atrial pacing pulses; and
    control atrial stimulation of the left atrial pacing pulses, by applying a pacing pulse at a short left inter-atrial delay, shorter than the coupling interval of sinus rhythm according to a stimulation protocol, the stimulation protocol comprising:
        after a first cardiac cycle without left atrial pacing, delivery of a premature left atrial stimulation pulse during a second immediately consecutive cardiac cycle, with application of a short left inter-atrial delay shorter than the coupling interval of sinus rhythm;
        delivery of a non premature left-atrial stimulation pulse during a third cardiac cycle immediately subsequent to the second cardiac cycle, with application of a left inter-atrial delay corresponding to the coupling interval of sinus rhythm;
    assess the atrioventricular interval between left atrial depolarization and ventricular depolarization during the second and third cardiac cycles, or the interventricular delay between two successive ventricular depolarizations;
    compare the atrioventricular interval thus evaluated to the atrioventricular interval in sinus rhythm, or the interventricular delay thus assessed to the interventricular delay in sinus rhythm; and
    control at least one parameter of the stimulation protocol according to the result of the comparison.

2. The device of claim 1, wherein the parameter that is controlled depending on the result of the comparison, is the short left inter-atrial delay.

3. The device of claim 2, wherein, if the atrioventricular interval increases above a given target value, or if the interventricular delay interval is less than the sinus rhythm coupling interval, the digital processor is further configured to:
    reduce of a step change the short left inter-atrial delay; then
    deliver a premature left atrial stimulation pulse during a subsequent cardiac cycle, with application of the short left inter-atrial delay reduced by one step.

4. The device of claim 3, wherein, if the atrioventricular interval does not increase beyond the target value, and if the interventricular delay remains equal to the sinus rhythm coupling interval, the digital processor is further configured to:
    increase by one variation step the short left inter-atrial delay; then
    deliver a premature left atrial stimulation pulse during a subsequent cardiac cycle, with application of the short left inter-atrial delay increased by one step.

5. The device of claim 1, further comprising a digital processor circuit configured to, on detection of a predetermined event:
    inhibit any delivery of left atrial pacing pulse during at least during one cardiac cycle;
    measure on at least one cardiac cycle the ventricular coupling interval; and
    store this coupling ventricular interval as the sinus rhythm coupling interval for the determination of the short left inter-atrial and left inter-atrial delays corresponding to the sinus rhythm coupling interval in subsequent cycles.

6. The device of claim 5, wherein the predetermined event is the expiry of a predetermined fixed time interval.

7. The device of claim 5, wherein the predetermined event is the detection of the exceeding of a predetermined threshold by the variation of the atrio-ventricular delay and/or of the atrial coupling interval and/or of the interventricular delay.

8. The device of claim 2, further comprising a digital processor circuit configured to:
    collect right atrial depolarization; and
    assess the variation, from one cardiac cycle to the following one(s), of the atrioventricular interval between the right atrial depolarization and the ventricular depolarization; and
    if the variation thus assessed exceeds a predetermined threshold, reduce by one variation step the short left inter-atrial delay.

9. The device of claim 1, wherein the device has no means for collecting and analyzing the endocardial acceleration.

10. A method for resynchronization of the contraction of the heart chambers, the method comprising:
    sensing ventricular depolarizations;
    sensing left atrial depolarizations; and
    controlling atrial stimulation to prematurely selectively output the left atrial pacing pulses, by applying a pacing pulse at a short left inter-atrial delay, shorter than the coupling interval of sinus rhythm according to a stimulation protocol, the stimulation protocol comprising:
        after a first cardiac cycle without left atrial pacing, delivery of a premature left atrial stimulation pulse during a second immediately consecutive cardiac cycle, with application of a short left inter-atrial delay shorter than the coupling interval of sinus rhythm;
        delivery of a non-premature left-atrial stimulation pulse during a third cardiac cycle immediately subsequent to the second cardiac cycle, with application of a left inter-atrial delay corresponding to the coupling interval of sinus rhythm;
    assessing the atrioventricular interval between left atrial depolarization and ventricular depolarization during the second and third cardiac cycles, or the interventricular delay between two successive ventricular depolarizations;

comparing the atrioventricular interval thus evaluated to the atrioventricular interval in sinus rhythm, or the interventricular delay thus assessed to the interventricular delay in sinus rhythm; and controlling at least one parameter of the stimulation protocol according to the result of the comparison.

11. The method of claim 10, wherein the controlled parameter is the short left inter-atrial delay.

12. The method of claim 11, further comprising modifying the short left inter-atrial delay interval if the atrioventricular interval increases above a given target value, or if the interventricular delay interval is less than the sinus rhythm coupling interval by:

reducing of a step change the short left inter-atrial delay; then delivering a premature left atrial stimulation pulse during a subsequent cardiac cycle, with application of the short left inter-atrial delay reduced by one step.

13. The method of claim 11, further comprising modifying the short left inter-atrial delay interval if the atrioventricular interval does not increase beyond the target value, and if the interventricular delay remains equal to the sinus rhythm coupling interval by:

increasing by one variation step the short left inter-atrial delay; then delivering a premature left atrial stimulation pulse during a subsequent cardiac cycle, with application of the short left inter-atrial delay increased by one step.

14. The method of claim 10, further comprising:
detecting a predetermined event;
inhibiting any delivery of left atrial pacing pulse during at least during one cardiac cycle;
measuring on at least one cardiac cycle the ventricular coupling interval; and
storing this coupling ventricular interval as the sinus rhythm coupling interval for the determination of the short left inter-atrial and left inter-atrial delays corresponding to the sinus rhythm coupling interval in subsequent cycles.

15. The method of claim 14, wherein the predetermined event is the expiry of a predetermined fixed timing interval.

16. The method of claim 14, wherein the predetermined event is the detection of the exceeding of a predetermined threshold by the variation of the atrio-ventricular delay and/or of the atrial coupling interval and/or of the interventricular delay.

17. A method of providing atrial stimulation for resynchronization of the heart chambers, comprising:

after a first cycle without stimulation, delivering a premature left atrial stimulation applied at a short left inter-atrial delay, shorter than the sinus rhythm coupling interval;

during the next cycle, delivering a non-premature left atrial stimulation;

comparing an atrioventricular interval between the left atrial depolarization and the ventricular depolarization to its value in sinus rhythm; and controlling the left inter-atrial delay.

18. The method of claim 17, wherein controlling the left inter-atrial delay comprises modifying the inter-atrial coupling delay if the atrioventricular interval increases above a given target value by:

reducing of a step change the short left inter-atrial delay; then delivering a premature left atrial stimulation pulse during a subsequent cardiac cycle, with application of the short left inter-atrial delay reduced by one step.

19. The method of claim 17, wherein controlling the left inter-atrial delay comprises modifying the left inter-atrial delay if the atrioventricular interval does not increase beyond the target value by:

increasing by one variation step the short left inter-atrial delay; then delivering a premature left atrial stimulation pulse during a subsequent cardiac cycle, with application of the short left inter-atrial delay increased by one step.

20. The method of claim 17, further comprising:
detecting a predetermined event;
inhibiting any delivery of left atrial pacing pulse during at least during one cardiac cycle;
measuring on at least one cardiac cycle the ventricular coupling interval; and
storing this coupling ventricular interval as the sinus rhythm coupling interval for the determination of the short left inter-atrial and left inter-atrial delays corresponding to the sinus rhythm coupling interval in subsequent cycles.

* * * * *